United States Patent [19]

Lempert et al.

[11] Patent Number: 4,559,406
[45] Date of Patent: Dec. 17, 1985

[54] PROCESS FOR THE PREPARATION OF AMINOLACTONE CARBOXYLIC ACID

[75] Inventors: Károly Lempert; Gábor Doleschall; József Fetter; Gyula Hornyák; József Nyitrai; Gyula Simig, all of Budapest; Károly Zauer, Szentendre, all of Hungary

[73] Assignee: Richter Gedeon Vegyeszeti Gyav R.T., Budapest, Hungary

[21] Appl. No.: 508,436

[22] Filed: Jun. 27, 1983

[30] Foreign Application Priority Data

Jul. 30, 1982 [HU] Hungary ................................. 2449

[51] Int. Cl.³ .......................................... C07D 309/30
[52] U.S. Cl. ................................ 549/291; 260/239 A; 260/330.9
[58] Field of Search ......................................... 549/291

[56] References Cited

U.S. PATENT DOCUMENTS

| | | | |
|---|---|---|---|
| 4,269,772 | 5/1981 | Melillo et al. | 549/291 |
| 4,282,148 | 8/1981 | Liu et al. | 549/291 |
| 4,287,123 | 9/1981 | Liu et al. | 549/291 |
| 4,344,885 | 8/1982 | Liu et al. | 549/291 |
| 4,349,687 | 9/1982 | Liu et al. | 549/291 |
| 4,360,684 | 11/1982 | Cvetovich et al. | 549/291 |

OTHER PUBLICATIONS

Houben-Weyl, Methoden der Organischen Chemie, vol. VI/2 (1963) pp. 588–589.
D. G. Melillo et al., Tetrahedron Letters, vol. 21 (1980) pp. 2783–2786.

Primary Examiner—Norma S. Milestone
Attorney, Agent, or Firm—Karl F. Ross; Herbert Dubno

[57] ABSTRACT

The invention relates to a process for the preparation of the compound of the formula I,

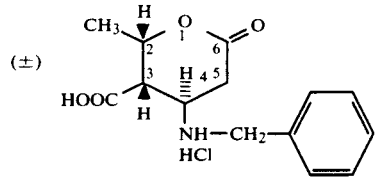

which comprises
(a₁) splitting off the ethylene ketal protecting group from the azetidinone derivative of the formula IVa,

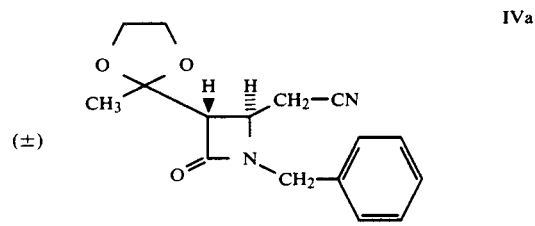

reducing the compound of the formula III thus obtained,

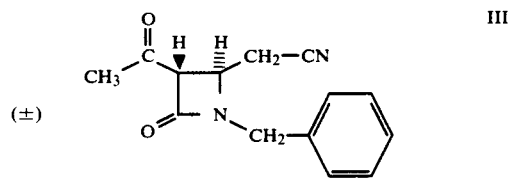

treating the resulting compound of the formula II

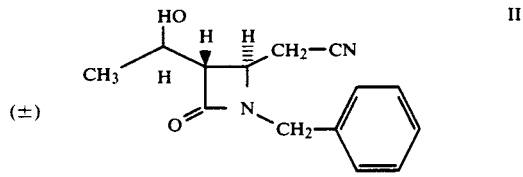

with concentrated aqueous hydrogen chloride solution; or (a₂) reducing the compound of the formula III, treating the compound of the formula II thus obtained with concentrated aqueous hydrogen chloride solution; or (a₃) treating the compound of the formula II with concentrated aqueous hydrogen chloride solution; and isolating the compound of the formula I thus obtained from the reaction mixture. The compound of the formula I is useful as an intermediate in the production of thienamycin, a highly potent antibiotic.

10 Claims, No Drawings

PROCESS FOR THE PREPARATION OF AMINOLACTONE CARBOXYLIC ACID

This invention relates to a new process for the preparation of the aminolactone-carboxylic acid of the formula I

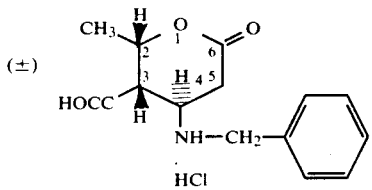

The compound of the formula I is useful as an intermediate in the production of thienamycin. This latter compound has been demonstrated to be a highly potent antibiotic (published German patent application No. 2,751,597). The key intermediate of the formula I, its preparation from diethyl-1,3-acetone dicarboxylate and the conversion thereof into thienamycin has been described by D. G. Melillo et al, Tetrahedron Letters 21, 2783-86 (1980).

Now it has been found that the compound of the formula I can be prepared by an original and operationally simple method via the new trans-intermediates of the formulae III and II.

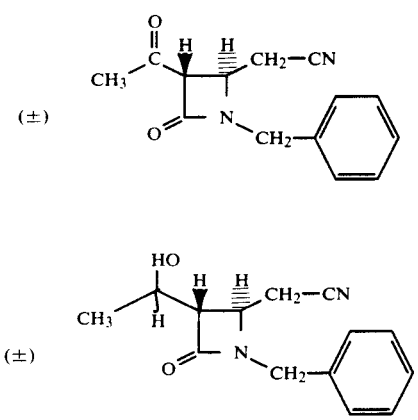

The new intermediates need not be isolated. The starting substance of the formula IVa

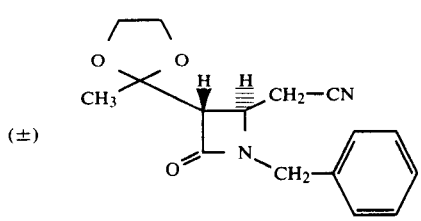

crystallizes well, the applied reagents are more readily available and the reaction steps are simpler than in the case of the known synthesis. Furthermore in the last reaction step only the compound of the formula I useful in the synthesis of (±)-thienamycin separates from the reaction mixture in a chemically uniform state.

According to a feature of the present invention there are provided the new compounds of the formulae II and III.

According to a further feature of the invention there is provided a new method for the preparation of the compound of the formula I, characterized by (a₁) splitting off the ethylene ketal protecting group from the azetidinone derivative of the formula (IVa), reducing the compound of the formula (III) thus obtained, treating the compound of the formula (II) thus obtained with concentrated aqueous hydrogen chloride solution; or (a₂) reducing the compound of the formula III, treating the compound of the formula II thus obtained with concentrated aqueous hydrogen chloride solution; or (a₃) treating the compound of the formula II with concentrated aqueous hydrogen chloride solution; and isolating the compound of the formula I thus obtained from the reaction mixture.

According to our previous experiments the starting substance of the formula IVa of trans configuration can be prepared by acylating a dialkyl-(N-benzylaminomalonate) of the formula X

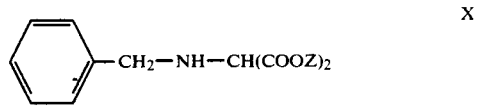

with diketene to the compound of the formula IX

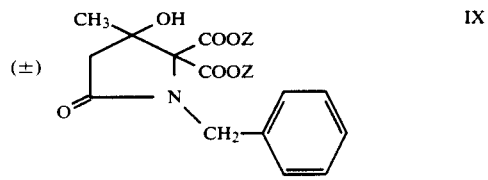

or into the tautomer thereof corresponding to the formula IXa

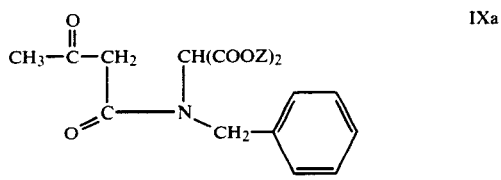

the compounds of the formulae IX and/or IXa are then converted into a compound of the formula VIII

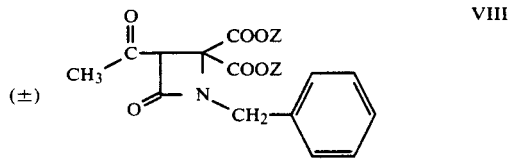

by adding simultaneously an alkali alcoholate and iodine, and the thus obtained compound of the formula VIII is reacted with ethylene glycol. The resulting compound of the formula VII

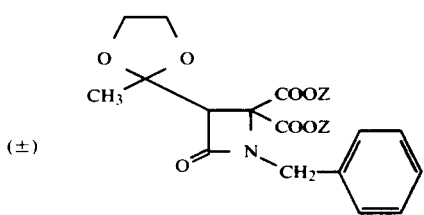

is then reacted with an alkali halide in the presence of water and dimethyl sulfoxide to obtain a mixture of the trans isomer of the formula VIa

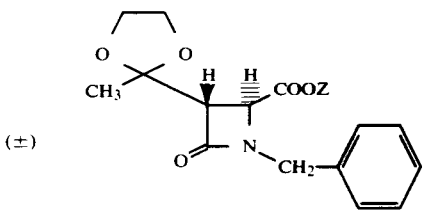

and the cis isomer of the formula VIb.

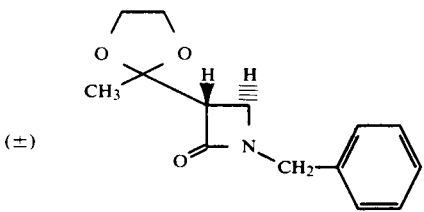

In the formulae X-VIa, VIb, Z represents a $C_{1-4}$ alkyl group.

The mixture of the isomers of the formulae VIa and VIb is then treated with an alkali tetrahydroborate (III) at a temperature between about 0° C. and room temperature. The resulting compound of the formula Va

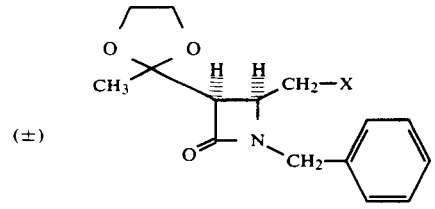

wherein X stands for a hydroxyl group, can be crystallized from the reaction mixture. The cis ester of the formula VIb can be obtained by subjecting the mother liquor to thin layer chromatographic separation. When reducing this latter compound with an alkali tetrahydroborate (III) at elevated temperatures, the trans derivative of the formula Va, wherein X is hydroxyl, is obtained (a transformation of the configuration takes place).

The compound of the formula Va, wherein X is hydroxyl, is then converted into a compound of the formula Va, wherein X is mesyl or tosyl, and this latter compound is converted into a compound of the formula Va, wherein X is halogen. When reacting this halo derivative with an alkali cyanide, the trans isomer of the formula IVa is obtained.

According to the process of the invention the ethylene ketal protecting group is first split off from the compound of the formula IVa. The ketal group is removed with a Broensted or Lewis acid, e.g. with a mineral acid, preferably with aqueous perchloric acid, under cooling. The reaction is preferably carried out in the presence of a ketone, preferably acetone, while the reaction is monitored by thin layer chromatography (adsorbent: Kieselgel a, according to Stahl, developing mixture: benzene-acetone 8:2). Then the reaction mixture is neutralized, and the thus-obtained new compound of the formula III is optionally isolated. It is preferable to perform the reduction of the reaction mixture without isolating the compound of the formula III.

The reduction is carried out with a complex metal hydride, preferably with sodium tetrahydroborate (III). The thus-obtained new compound of the formula II may be isolated from the reaction mixture by chromatography, but it is preferable to carry out the reaction without isolating the compound of the formula II.

The new compound of the formula II, which is a racemic mixture of two epimers, is then converted into the lactone of the formula I. The reaction is carried out at elevated temperatures, in the presence of concentrated aqueous hydrogen chloride solution.

The compound of the formula I thus obtained separates from the reaction mixture.

The invention is illustrated by the following Examples of non-limiting character:

EXAMPLE 1

Preparation of (2RS, 3RS, 4SR)-4-(benzyl-amino)-2-methyl-6-oxo-tetrahydropyran-3-carboxylic acid hydrochloride (I)

0.85 g (3.5 mmoles) of (3RS, 4SR)-1-benzyl-4-(cyanomethyl)-3-(1'-hydroxyethyl)-2-azetidinone of the formula II (the mixture of two 1'-epimers) are boiled in 10 ml of concentrated aqueous hydrogen chloride solution for 3 hours The separated crystalline product is filtered off and dried.

Yield: 0.52 g (50%) of the named compound.

M.p.: 163° to 164° C. (decomp.)

$^1$H-NMR(DMSO-$d_6$+CDCl$_3$): $\delta$=1.31 d (3H, J=5.6 Hz); 3.08 dd+3.28 dd (2H, J=15.5 Hz and 8.0 Hz; and 15.5 Hz and 9.0 Hz, respectively); 3.38 dd (1H, J=3 Hz and 3.5 Hz); 4.04 dt (1H, J=3 Hz and ~8 Hz); 4.21 s (2H); 5.24 dq (1H, J=3.5 Hz and 6 Hz); 7.32–7.73 m (5H).

The starting substances of Example 1 is prepared as follows:

(a) Into a mixture of 59.2 g (41.2 ml; 0.199 moles) of diethyl bromomalonate and 22.5 g (31.5 ml; 0.225 moles) of triethylamine, 24 g (24.3 ml; 0.207 moles) of benzylamine are dropped under intensive external cooling with ice water and vigorous stirring. A mass difficult to stir is obtained. It is stirred for 15 hours, trituretred with 100 ml of ether, the separated crystalline product is filtered, ethanol containing hydrogen chloride is dropped to the filtrate, the separated crystalline product is filtered off and dried.

Yield: 23 g (31% of diethyl N-benzylaminomalonate hydrochloride

M.p.: 146° to 148° C. (decomp.)

(b) A mixture of 33.3 g (0.125 moles) of diethyl (N-benzylaminomalonate) and 11.6 ml (0.152 moles; 12.8 g) of diketene are boiled in 40 ml of glacial acetic acid for half an hour. The solution is then evaporated, the residual oil is triturated with 150 ml of water, shaken twice with 80 ml of dichloromethane, dried over magnesium sulfate and filtered. The solution is evaporated to about a fourth of its original volume and the product is precipitated with petroleum ether.

Yield: 27.5 g (63%) of (±)-diethyl (N-benzyl-3-hydroxy-3-methyl-5-oxo-2,2-pyrrolidine carboxylate) of the formula (IX) and/or its tautomer of the formula (IXa).

M.p.: 85° to 86° C. (ethyl acetate-petroleum ether)

Analysis: $C_{18}H_{23}NO_6$ (349.37); Calculated: C %=61.88, H %=6.63, N %=4.01; Found: C %=61.74, H %=6.78, N %=4.30.

IR(KBr): 3400, 1755, 1725, 1685 cm$^{-1}$ $^1$H-NMR (CDCl$_3$): δ1.12 t (6H), 1.51 (3H), 2.68 s (2H), 3.05–4.25 m (5H), 4.8 s (2H), 7.2 s (5H).

(c) 10 g (28.6 mmoles) of (±)-diethyl-(N-benzyl-3-hydroxy-3-methyl-5-oxo-2,2-pyrrolidine dicarboxylate) of the formula IX and/or the tautomer thereof are suspended in 50 ml of dry ether, and the solutions of 1.97 g (85.8 moles) of sodium metal in 45 ml of anhydrous ethanol and 7.26 g (28.6 mmoles) of iodine in 50 ml of dry ether are added simultaneously, through two separate dropping funnels, under vigorous stirring and external cooling with ice water. The mixture is poured onto 150 ml of saturated aqueous sodium chloride solution in which 2 g of sodium hydrogen sulfite have been dissolved. The organic phase is separated, the aqueous phase is shaken twice with 50 ml of ether each, dried over magnesium sulfate, filtered and the filtrate is evaporated. The residual oil is crystallized from the mixture of 2-propanol and petroleum ether.

Yield: 8 g (80%) of (±)-diethyl-(3-acetyl-1-benzyl-4-oxo-2,2-azetidine dicarboxylate) of the formula (VIII).

M.P.: 55° to 56° C. (2-propanol-petroleum ether)

$^1$H-NMR (CDCl$_3$): δ1.08 t (3H), 1.22 t (3H), 2.3 s (3H), 3.7–4.3 m (4H), 4.45 d (1H), 4.8 s (1H), 7.28 s (5H).

Analysis: $C_{18}H_{21}NO_6$ (347.36); Calculated: C %=62.24, H %=6.09, N %=4.03; Found: C %=62.27, H %=5.70, N %=4.08.

IR(KBr): 2950, 1745, 1720, 1705 cm$^{-1}$.

(d) To a solution of 24.8 g (71 mmoles) of (±)-diethyl (3-acetyl-1-benzyl-4-oxo-2,2-azetidine dicarboxylate) and 15.8 ml (17.7 g; 284 mmoles) of ethylene glycol in 75 ml of dry dioxane 26.4 ml (30.4 g; 213 mmoles) of boron trifluoride-diethyl etherate are dropped under vigorous stirring and external cooling with ice water The mixture is allowed to stand at room temperature for one day and stirred from time to time. Then 60.9 g (123 mmoles) of Na$_2$CO$_3$.10 H$_2$O are added slowly, under stirring and external cooling with ice water, and the mixture is stirred for another 15 minutes. Then 150 ml of water and 150 ml of ether are added and the phases are separated. The aqueous phase is shaken twice with 50 ml of ether each. The ethereal phase is dried over magnesium sulfate, filtered and evaporated. To the residual oil the compound of the formula VII 5 g (85 mmoles) of sodium chloride, 2.56 ml (142 mmoles) of water and 30 ml of diethyl sulfoxide are added, and the mixture is stirred on an oil bath at 180° C. until completion of the reaction (about 15 hours, monitored by thin layer chromatography; adsorbent: Kieselgel G, according to Stahl; eluent: benzene-acetone 8:2). The mixture is poured onto 100 ml of concentrated aqueous sodium chloride solution and shaken three times with 50 ml of ether. The ethereal phase is clarified with charcoal, dried over magnesium sulfate, filtered and evaporated. To the residual oil (the mixture of the compounds of the formulae VIa and VIb 80 ml of aqueous methanol are measured and 3.8 g (100 mmoles) of sodium tetrahydroborate (III) are added slowly, under external cooling with ice water, and the mixture is stirred at room temperature for 1 hour. Then it is poured onto 200 ml of saturated aqueous sodium chloride solution, shaken first with 100 ml then twice with 50 ml of ether, the ethereal solution is dried over magnesium sulfate and evaporated. The residual oil is triturated with ether and crystallized. The crystals are filtered off, dried and the ethereal mother liquor is put aside Yield: 7.4 g (37% of (±)-trans-1-benzyl-4-(hydroxymethyl)-3-2-methyl-1,3-dioxalan-2-yl)-2-azetidinone of the formula (Va) wherein X is hydroxyl.

M.p.: 87° to 88° C. ethylacetate-petroleum ether.

Analysis: $C_{15}H_{19}NO_4$ (277.31); Calculated: N %=5.05; Found: N % =4.78.

IR (KBr): 3350, 1840 cm$^{-1}$ $^1$H-NMR (CDCl$_3$): δ1.40 s (3H), 2.0 b s (1H), 3.31 d (1H, J=2.5 Hz), 3.43–3.80 m (3H), 3.9–4.1 m (4H), 4.26+4.63 (2H, AB, J=15 Hz); 7.32 s (5H).

The mother liquor put aside when filtering the compound of the formula Va, wherein X is hydroxyl, is then evaporated and the residue is purified by column chromatography (adsorbent: Kieselgel 60; φ0.063–0.200 mm, eluent: benzene→benzene-acetone 8:2.

Yield: 2.95 g of (±)-ethyl cis-1-benzyl-3-(2-methyl-1,3-dioxolan-2-yl)-4-oxo-2-azetidine carboxylate of the formula VIb, wherein Z is ethyl.

$^1$H-NMR (CDCl$_3$): δ1.28 t (3H, J=7.2 Hz), 1.43 s (3H), 3.75 d (1H, J=6.5 Hz), 3.9–4.1 m (3H), 4.24 q (2H, J=7.2 Hz), 4.22+4.90 (2H, AB, J=15 Hz), 7.15–7.40 m (5H). 2.6 g (8.2 mmoles) of (±)-ethyl cis-1-benzyl-3-(2-methyl-1,3-dioxolan-2-yl)-4-oxo-2-azetidine carboxylate are dissolved in 20 ml of methanol, 0.62 g (16.4 mmoles of sodium tetrahydroborate(III) are added and the mixture is boiled for one hour. Then further 0.62 g (16.4 mmoles) of sodium tetrahydroborate(III) are added, and the mixture is boiled for another one hour. The solution is poured onto 100 ml of saturated sodium chloride solution, shaken three times with 40 ml of ether each, dried over magnesium sulfate, filtered and the filtrate is evaporated. The residue is triturated with water.

Yield: 0.8 g (35%) of (±)-trans-1-benzyl-4-(hydroxymethyl)-3-(2-methyl-1,3-dioxolan-2-yl)-2-azetidinone Va, wherein X stands for hydroxyl. The physical constants of the compound are identical to those of the primary product.

(e) To a solution of 7.4 g (26.7 mmoles) of (±)-trans-1-benzyl-4-(hydroxymethyl)-3-(2-methyl-1,3-dioxolan-2-yl)-2-azetidinone in 20 ml of pyridine 2.5 ml (32 mmoles) of mesyl chloride are dropped within 10 minutes, under external cooling with ice water, and the mixture is stirred at 0° C. for one hour. 100 ml of water are added, the separated crystalline product is filtered and dried.

Yield: 7.7 g (81%) of (±)-trans-1-benzyl-3-(2-methyl-1,3-dioxolan-2-yl)-4-(mesyloxymethyl)-2-azetidinone Va, wherein X is -O-SO$_2$-CH$_3$.

M.p.: 87° to 88° C. (ethyl acetate-petroleum ether).

Analysis: $C_{16}H_{21}NO_6S$ (355.40); Calculated: O %=54.07, H %=5.96, N %=3.94; Found: O %=53.86, H %=6.02, N %=3.99.

IR (KBr): 1840 cm$^{-1}$ $^1$H-NMR (CDCl$_3$): δ1.40 s (3H), 2.88 s (3H), 3.30 d (1H, J=2.5 Hz), 3.60–3.75 m (1H), 3.98 (center) m (4H), 4.14+4.34 (2H, dAB, J=3.6 Hz, 5.5 Hz and 11 Hz), 4.20+4.72 (2H, AB, J=15 Hz), 7.31 s (5H).

(f) 7.5 g (21 mmoles) of (±)-trans-1-benzyl-3-[2-methyl-1,3-(2-methyl-1,3-dioxolan-2-yl]-4-(mesyloxymethyl)-2-azetidinone and 12.6 g (84 mmoles) of sodium iodide are dissolved in 40 ml of dry acetone and the solution is boiled for 4 hours, under stirring. The mixture is evaporated to dryness. The residue is dissolved in 50 ml of water and the solution is extracted three times with 30 ml of dichloromethane each. The dichloromethane solution is dried over magnesium sulfate, filtered and evaporated.

Yield: 7.7 g (94%) of (±)-trans-1-benzyl-4-(iodomethyl)-3-(2-methyl-1,3-dioxolan-2-yl)-2-azetidinone (Va), wherein X is iodine.

IR: 1850 cm$^{-1}$ $^1$H-NMR (CDCl$_3$): δ1.42 s (3H), 3.20 d (1H, J=2 Hz), 3.15+3.30 (2H, d AB, J=4.0 Hz, 6.0 Hz and 11 Hz), 3.35–3.55 m (1H), 3.98 (center) m (4H), 4.12+4.87 (2H, AB, J=15 Hz), 7.31 s (5H).

(g) 4.3 g (11.1 mmoles) of (±)-trans-1-benzyl-4-(iodomethyl)-3-(2-methyl-1,3-dioxolan-2-yl)-2-azetidinone and 2.18 g (44.4 mmoles) of sodium cyanide are dissolved in 10 ml of dry dimethylformamide, the mixture is allowed to stand at 0° C. to 5° C. for a few days and stirred from time to time. The reaction is monitored by thin layer chromatography (adsorbent: Kieselgel G, according to Stahl, eluent: benzene-acetone 8:2). The mixture is poured onto 60 ml of saturated sodium chloride solution, shaken three times with 40 ml of ether each, the ethereal solution is dried over magnesium sulfate, filtered and the filtrate is evaporated.

Yield: 2.88 g (90%) of (±)-trans-1-benzyl-4-(cyanomethyl)-3-(2-methyl-1,3-dioxolan-2-yl)-2-azetidinone of the formula (IVa).

IR (KBr): 1860 cm$^{-1}$.

M.p.: 64° to 65° C. (ethyl acetate-petroleum ether)

$^1$H-NMR (CDCl$_3$): δ1.41 s (3H), 2.51 d (2H, J=5.6 Hz), 3.29 d (1H, J=2.5 Hz), 3.63 dt (J=2.5 and 5.6 Hz), 3.96 (center) m (4H), 4.20+4.72 (2H, AB, J=15 Hz), 7.32 s (5H).

(h) To a solution of 1.82 g (6.4 mmoles) of (±)-trans-1-benzyl-4-(cyanomethyl)-3-(2-methyl-1,3-dioxolan-2-yl)-2-azetidinone in 20 ml of acetone 1.35 ml of 70% aqueous perchloric acid solution are added under stirring and external cooling with ice water. Then 1.67 g of sodium hydrogen carbonate are added, and the neutral solution is evaporated. The residue is dissolved in 20 ml of methanol under external cooling with ice water, 0.4 g (10.5 mmoles) of sodium tetrahydroborate(III) are added, and the mixture is stirred for 15 minutes. Then it is poured onto 100 ml of saturated aqueous sodium chloride solution, shaken three times with 30 ml of dichloromethane each, dried over magnesium sulfate and evaporated. The residual oil is separated by thin layer chromatography (adsorbent: Kieselgel 60, PF 254+366, eluent: benzene-acetone 8:2.

Yield: 0.55 g (30%) of the compound of the formula (IVa), which may be recirculated, furthermore 0.90 g (58%) of (3RS, 4SR)-1-benzyl-4-(cyanomethyl)-3-(1'-hydroxyethyl)-2-azetidinone of the formula (II).

$^1$H-NMR (CDCl$_3$): δ1.28 d+1.31 d (3H, J=7 Hz), 2.25 b s (1H), 2.50 (center) m (2H), 3.02 dd+3.09 dd (1H; J=2.2 Hz and 5 Hz), 3.68 dt+3.81 dt (J=2.2 and 5.5 Hz), 4.00–4.25 m (1H), 4.23+4.60 (2H, AB, J=15 Hz), 7.32 s (5H).

EXAMPLE 2

Preparation of (2RS, 3RS, 4SR)-4-(benzylamino)-2-methyl-6-oxo-tetrahydropyran-3-carboxylic acid hydrochloride (I)

To a solution of 2 g (7 mmoles) of (±)-trans-1-benzyl-4-(cyanomethyl)-3-(2-methyl-1,3-dioxolan-2-yl)-2-azetidinone, the compound of the formula (IVa) in 25 ml of acetone 1.49 ml of 70% aqueous perchloric acid solution are added under stirring and external cooling with ice water, and the mixture is stirred for 4 hours at 0° C. Then 1.84 g of sodium hydrogen carbonate are added and the neutral solution is evaporated. The residue is dissolved in 25 ml of methanol, and 0.44 g (11.6 mmoles) of sodium tetrahydroborate(III) are added. The mixture is stirred for 15 minutes, poured onto 100 ml of saturated aqueous sodium chloride solution, shaken three times with 30 ml of dichloromethane, dried over magnesium sulfate and evaporated.

The residual oil is boiled with 20 ml of concentrated aqueous hydrogen chloride solution for 3 hours, clarified with charcoal and the filtrate is cooled. The separated crystalline product is filtered off, dried under an infrared lamp, washed with ether and dried again.

Yield: 0.72 g (35%) of (2RS, 3RS, 4SR)-4-(benzylamino)-2-methyl-6-oxo-tetrahydropyran-3-carboxylic acid hydrochloride of the formula I.

M.p.: 161°–162° C. (decomp.).

We claim:

1. A process for the preparation of a salt of the Formula (I)

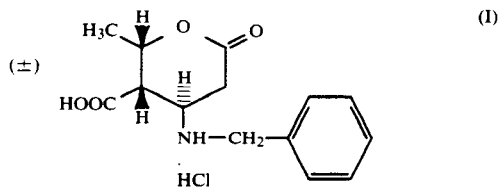

which comprises the steps of:

(a) splitting off the ethylene ketal protecting group from an azetidinone derivative of the Formula (IVa)

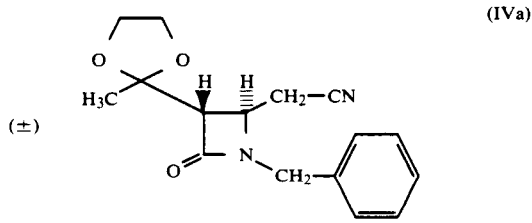

to produce a compound of the formula (III)

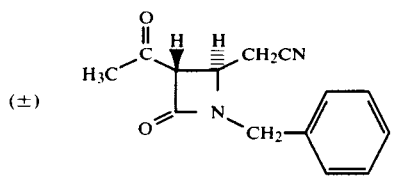

(b) reducing the compound of the Formula (III) to yield a compound of the Formula (II)

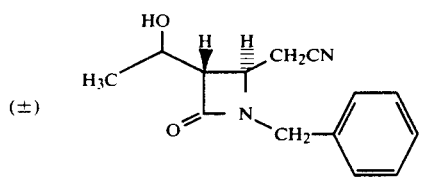

and (c) treating the compound of the Formula (II) with concentrated aqueous hydrogen chloride solution to yield the desired product.

2. The process defined in claim 1, wherein following step (c) the desired product of the Formula (I) is isolated from the reaction mixture.

3. the process defined in claim 1 wherein in step (a) the protecting group is split off with a mineral acid.

4. The process defined in claim 3 wherein the protecting group is split off in the presence of a ketone.

5. The process defined in claim 1, wherein in step (b) the reduction is carried out with a complex metal hydride.

6. A process for the preparation of a salt of the Formula (I)

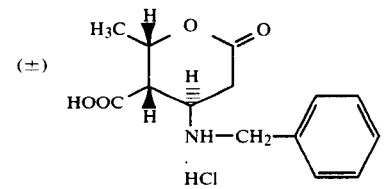

which comprises the steps of:

(a) reducing a compound of the Formula (III)

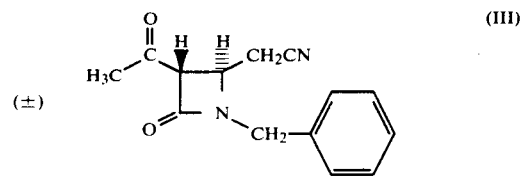

to yield a compound of the Formula (II)

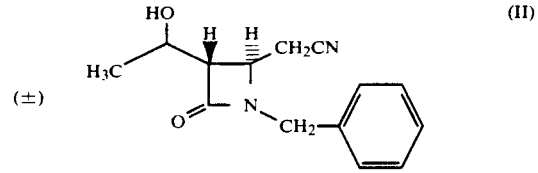

and (b) treating the compound of the Formula (II) with concentrated aqueous hydrogen chloride solution to yield the desired product.

7. The process defined in claim 6 wherein in step (a) the reduction is carried out with a complex metal hydride.

8. The process defined in claim 6 wherein following step (b) the desired product of the Formula (I) is isolated from the reaction mixture.

9. A process for the preparation of a salt of the Formula (I)

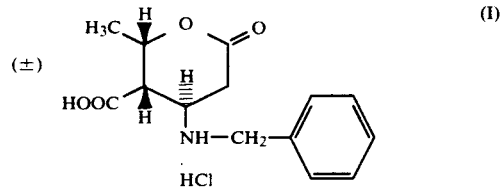

which comprises the step of treating a compound of the Formula (II)

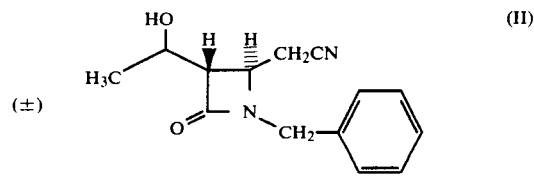

with concentrated aqueous hydrogen chloride solution to yield the desired product.

10. The process defined in claim 9 wherein the desired product of the Formula (I) is isolated from the reaction mixture.

* * * * *